United States Patent [19]

Sommer et al.

[11] 3,953,533
[45] Apr. 27, 1976

[54] PROCESS FOR THE HYDRATION OF OLEFINS TO ALCOHOLS

[75] Inventors: August Sommer, Herne; Martin Urban, Gelsenkirchen-Buer, both of Germany

[73] Assignee: Veba-Chemie Aktiengesellschaft, Gelsenkirchen-Buer, Germany

[22] Filed: Jan. 11, 1974

[21] Appl. No.: 432,727

[30] Foreign Application Priority Data
Jan. 11, 1973   Germany............................ 2301208

[52] U.S. Cl. ................................................ 260/641
[51] Int. Cl.² ........................................ C07C 29/04
[58] Field of Search .................................... 260/641

[56] References Cited
UNITED STATES PATENTS

| | | | |
|---|---|---|---|
| 2,148,288 | 2/1939 | Bent.............................. | 260/641 X |
| 3,686,334 | 8/1972 | Britton........................... | 260/641 |
| 3,793,379 | 2/1974 | Rosscup et al................. | 260/641 |

*Primary Examiner*—Bernard Helfin
*Attorney, Agent, or Firm*—Burgess, Dinklage & Sprung

[57] ABSTRACT

Olefins having two and three carbon atoms are hydrated in the presence of phosphoric acid-containing supported catalysts to the corresponding alcohols. For the hydration of olefins having two carbon atoms, the molar ratio of water to olefin is in the range of about 0.1–0.3 : 1, the reaction temperatures in the range of about 190°–230°C, and the reaction pressure is in the range of about 60–80 atmospheres gauge. For the hydration of olefins having three carbon atoms, the molar ratio of water to olefin is in the range of about 0.1–0.3 : 1, the reaction temperatures in the range of about 140°–170°C and the reaction pressure is in the range of about 20–45 atmospheres gauge. The only by-products which form in addition to the raw alcohol under these conditions are steam-volatile (water soluble) by-products which are separated from the raw alcohol in a washing extraction zone. The by-products are recycled in aqueous solution without organic phase to the hydration in the state in which they are produced at the top of the washing extraction zone after separating unreacted olefin.

4 Claims, 1 Drawing Figure

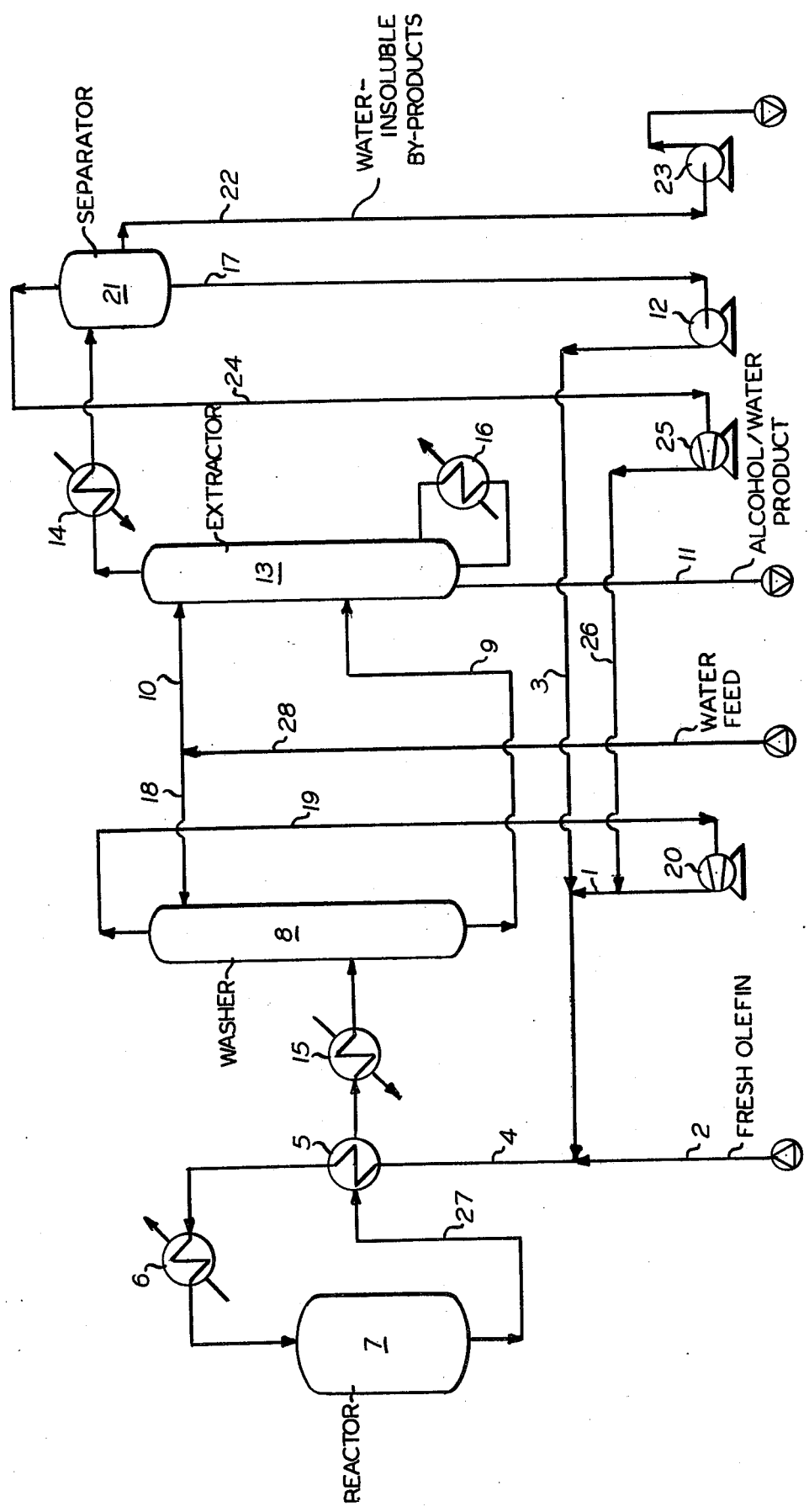

PROCESS FOR THE HYDRATION OF OLEFINS TO ALCOHOLS

BACKGROUND

This invention relates to a simplified, economical process for the production and refinement of alcohols having two and three carbon atoms wherein: the molar water-to olefin ratio is kept very small at relatively low temperature; by-products form in low concentration and are mostly easy to separate from the alcohol; and the water required in the hydrating process consists mostly of vapor condensate which is recycled directly into the process together with by-products that are in solution.

The catalytic hydration of ethylene at temperatures of especially 270°–290°C and pressures of especially 60 to 80 atmospheres gauge, and of propylene at temperatures of especially 170° to 240°C and pressures of especially 25 to 40 atmospheres gauge has long been known and is applied on a large technical scale. The molar water ratios (water to olefin) are between 0.6 and 1.0 : 1 in the ethanol process and 0.4 to 1.0 : 1 in the isopropanol process. The preferred catalyst is phosphoric acid on various support materials such as bentonite, diatomaceous earth, aluminum silicates and the like.

Conducting the reaction under the above-stated conditions of the prior art causes the formation with a high percentage of process water and high energy costs, of by-products consisting essentially of ether, aldehydes, ketones, butanols, higher secondary and tertiary alchols and higher hydrocarbons. Since these by-products cannot be completely separated by extractive distillation from the corresponding alcohol, namely ethanol or isopropanol as the case may be, purification of the raw alcohol produced has to be performed both by extraction and by distillation at high energy costs and investment costs if the quality requirements are high. This is especially true for secondary and tertiary higher alcohols which cannot be completely separated from the desired products. On the other hand, even though there is a certain market for these higher alcohols, the recovery of the by-products is unprofitable on account of the high costs, so that they have to be discarded or burned. Thus, depending on the activity of the catalyst and the manner in which it is used, 5 to 8 percent of the olefin put in (ethylene or propylene) is reacted to by-products and thus is largely wasted.

SUMMARY

It is therefore an object of the invention to provide a process for the synthesis of alcohol, in which virtually exclusively those by-products are formed which can easily be separated by simple washing extraction from the alcohol that is produced, and furthermore are produced in the reaction stage only at a low equilibrium concentration. The by-products formed in the process of the invention are less than 1% with reference to the alcohol formed for both ethanol and isopropanol.

It has quite surprisingly been found that, if certain reaction conditions are maintained as regards temperature, pressure and molar ratio of water to olefin, the only impurities that form in the alcohol synthesis are easily separable by washing, and that if the water-soluble impurites are recycled to the reactor with the wash water only a very slight further formation of these by-products occurs.

The subject matter of the invention is therefore a process for the hydration of olefins having 2 and 3 carbon atoms in the presence of supported catalysts containing phosphoric acid to form the corresponding alcohols. For the hydration of olefins having two carbon atoms, the molar ratio of water to olefin is in the range of about 0.1–0.3 : 1, the reaction temperature is in the range of about 190°–230°C, and the reaction pressure is in the range of about 60–80 atmospheres gauge. For the hydration of olefins having 3 carbon atoms, the molar ratio of water to olefin is in the range of about 0.1–0.2 : 1, the reaction temperature is in the range of about 140°–170°C and the reaction pressure is in the range of about 20–45 atmospheres gauge. The only by-products which form in addition to the alcohol under these conditions are steam-volatile (water soluble) by-products which are separated from the alcohol in a wash extraction column and are recycled in an aqueous solution containing no organic phase to the process in the state in which they exist at the head of the wash column after separation of the olefin.

DESCRIPTION OF THE DRAWING

The present inventors will be more fully understood from the following description taken in conjunction with the accompanying drawing which is a flow diagram for carrying out the process of the invention.

DESCRIPTION

In the hydration of ethylene to ethanol the following conditions are employed:

| | |
|---|---|
| Temperature range | 190–230°C |
| Molar ratio, water : ethylene | 0.1–0.3 : 1 |
| Reaction pressure | 60–80 atm. gauge |

In the hydration of propylene to isopropanol the conditions are as follows:

| | |
|---|---|
| Temperature range | 140–170°C |
| Molar ratio, water : Propylene | 0.1–0.2 : 1 |
| Reaction pressure | 20–45 atm. gauge |

Under the above conditions the only impurites that are produced, in contrast to known processes, are those which are easy to separate by washing extraction. If the impurities in aqueous solution separated in the washing extraction together with a large amount of water are recycled in the state in which they exist at the top of the washing extraction column, but without any organic layers that may separate, then, after the attainment of an equilibrium, the total amount of impurities which are formed anew is far less than 1 percent. By this process step it is possible to improve the selectivity of the reaction both in the synthesis of ethanol and in the synthesis of isopropanol to such an extent that process yields above 99.5 percent of the theory are achieved based on consumed olefin.

The reaction mixture expanded from the synthesis circuit, consisting substantially of the alcohol that is formed, ether, aldehydes, ketone, hydrocarbon, olefin and water, is released into an extraction column for the purpose of separating the by-products and the unreacted olefin retained by dissolution in the reaction mixture. The amounts of energy needed in the extraction column for the preparation of the sump product, which is obtained free of by-products, in the form of a mixture of about 10 percent ethanol or isopropanol in water, are adjusted to 50 to 150 kg of steam per 100 liters of pure alcohol, the ratio of heating steam, input and wash water being established such that the vapors rising from the topmost tray of the column will have an alcohol content of only 2 to 10 percent with respect to the mixture of alcohol, by-products and water. In addition, olefin which is not condensable under the given reaction conditions emerges at the top and, after condensation in a separating tank, is separated from the mixture of alcohol, water and by-products and recycled to the synthesis.

Since the water vapor content of the vapors, with respect to the mixture of by-products, alcohol and water that is then present amounts to more than 85 percent, it is substantially water vapor that emerges, together with the by-products, from the top of the extraction column. If this dilute mixture of by-products (about 8.5 percent), alcohol (about 3 percent) and water (about 88.5 percent) is recycled into the synthesis, the total amount, or at least a large percentage, of the process water required is thus made available. Since the above-mentioned wash water comes from an apparatus connected to the output, which serves for dewatering of the alcohol, a virtually closed water circulation is available for the above-named reaction and purification apparatus. That is to say, in the case of the ethanol process, if 0.8 to 2.4 $m^3$ of process water per ton of ethaol is used in accordance with the molar ratio of water to olefin of 0.1–0.3 : 1, and in the case of the isopropanol process, if 0.65 to 1.3 $m^3$ of the process water per ton of isopropanol is used corresponding to a molar ratio of water to olefin of 0.1 to 0.2 : 1, the amount of process water required by the synthesis can be provided by the water recycled with the by-products alone, especially in the preferred lower molar operating range.

Therefore, by recycling the top product from the extraction column in the form of an aqueous solution of by-products without any organic phase, not only is the yield and selectivity of the process substantially improved, but also the production costs are considerably reduced through the elimination of the need for fresh process water. As a result of the better selectivity of the hydration reaction at low reaction temperatures, but owing to the substantial increase in the formation of ether (caused by a shift of the equilibrium), operation at low temperatures and low water-to-olefin ratios will be economical only if, by the recycling of especially ether and other by-products, the concentration of these components upon entering the reactor is already close to the equilibrium reaction and thus no further formation takes place. In this manner, a virtually closed circulation of by-products is achieved in addition to the above-mentioned closed water circulation.

It is advantageous, furthermore, as already mentioned, that the unreacted olefin from the expansion at the head of the extraction column can be separated from the aqueous solution of the by-products and then be fed into the synthesis.

The advantages of the process of the invention are summarized as follows:

a. The yield of the synthesis process with reference to ethylene reacted to ethanol or propylene reacted to isopropanol increases to values of 99.5 percent of the theory.
b. The end-products in the form of aqueous ethanol or isopropanol are prepared exclusively by purification through washing extraction, preferably in the course of expansion. They are of very high quality.
c. A considerable reduction of investment costs is achieved, because in the first place smaller surface areas are required for the heat exchange for the countercurrently heated reactor input gases or cooled reactor output gases, as the case may be, at low reaction temperature and low process watr consumption (low molar ratio), and secondly one achieves a saving of two additional distillation columns for the separation of hydrocarbons and higher alcohols and aldehydes.
d. A considerable reduction of the cost of power and auxiliary materials, since the processes are operated at comparatively extremely low temperatures and molar ratios of water to olefin, and thus, as stated, they are substantially more selective. The procedure, however, would be uneconomical due to the recycling of the by-products, especially ether, which form in an aqueous solution — without any organic phase — in the same state in which they are produced in the washing extraction, were it not for the fact that the further formation of these by-products, especially ether, in the reactor were not wholly or partially prevented.
e. Corrosion and the problem of the clogging of synthesis apparatus (mainly in the superheated region) are considerably reduced by the fact that, at the low temperature level, less acid leaves the reaction chamber and hence fewer of the components of the catalyst support which are soluble in this acid.

The process will now be described with reference to the drawing. Unreacted olefin 1 and fresh olefin 2 are mixed with the solution of by-products in water 17 drawn from the top of the extraction column 13, which is returned to the synthesis by pump 12 through line 3. The mixture passes through line 4 and heat exchanger 5 and on through the superheater 6 into the reactor 7.

The reaction mixture charged with the alcohol, consisting of unreacted olefin, alcohol, by-products and unreacted process water, is fed through line 27 to the heat exchanger 5 where it is cooled insofar as possible in order to condense as much alcohol as possible out of the reaction mixture. After passing through an aftercooler 15 the two-phase mixture enters the gas washer 8 in which the unreacted olefin is washed virtually free of alcohol with water from line 18.

The olefin washed out leaves the gas washer through line 19 as recirculation gas and is returned to the reaction system by the circulating compressor 20.

In addition to the produced alcohol, by-products and water (unreacted process water and wash water), the sump product 9 of the gas washer contains dissolved olefin under pressure which gasses out of the liquid upon expansion in the extraction column 13. The extraction column 13 is heated by quantities of vapor in the recirculation evaporator 16 in a manner such that a mixture of alcohol (about 10 percent) and water, free of by-products and olefin, leaves the column sump through line 11. To dewater the alcohol the product in line 11 is delivered to a separate apparatus provided for this purpose.

In addition to the wash water 18 which is used in the gas washer 8, additional water is introduced into the process from the above-mentioned alcohol dewatering apparatus through line 28 and delivered through line 10 to the extraction column. The water washed vapors in the column are partially condensed in the condenser 14 and delivered to the separator 21. From this separator the non-liquefied olefin is taken through line 24 as top product, suitably compressed by recycled gas compressor 25 and added through line 26 to the circulated gas from compressor 20.

Water-insoluble by-products, which decant in separator 21, are taken from a lateral outlet through line 22 and delivered by pump 23 for the application for which they are intended.

EXAMPLES

EXAMPLE 1

The synthesis products of known direct hydration processes for the production of ethanol and isopropanol contain by-products which form up to the following amounts with reference to the alcohol that is to be formed:

(a-1) Ethanol Process (prior art)
Reaction Conditions:
  Reaction pressure 70 atompsheres gauge
  Reaction temperature: 280°C
  Molar ratio, water : ethylene 0.6 : 1
  Circulating gas 1000 Nm$^3$/h per m$^3$ of catalyst
  Type of catalyst: H$_3$PO$_4$ on acid-treated bentonite supports per W. German Pat. No. 1,156,772

| By-Products: | |
|---|---|
| Diethyl ether | 3.0 wt-% |
| Hydrocarbons (up to C$_6$) | 1.5 wt-% |
| Acetaldehydes | 1.5 wt-% |
| Butanols | 1.0 wt-% |
| Others (polymers) | 1.5 wt-% |

(b-1) Isopropanol Process (prior art)
Reaction Conditions:
  Reaction pressure 40 atmospheres gauge
  Reaction temperature 240°C
  Molar ratio, water : propylene 0.4 : 1
  Circulating gas 800 Nm$^3$/h per m$^3$ of catalyst
  Catalyst type: H$_3$PO$_4$ on acid-treated Bentonite supports per W. German Pat. No. 1,156,772

| By-Products: | |
|---|---|
| Diisopropyl ether | 3.0 wt-% |
| Hydrocarbons (up to C$_6$) | 2.0 wt-% |
| Higher alcohols | 2.0 wt-% |
| Acetone | 0.5 wt-% |
| Others (polymers) | 0.5 wt-% |

By means of operating conditions altered in accordance with the invention, such as
  1. Lower reaction temperatures and
  2. Lower molar ratios of water to olefin, the composition and quantity of the by-products changes as follows:

(a-2) Ethanol Process (invention)
Reaction Conditions:
  Reaction pressure 70 atmospheres gauge
  Reaction temperature 220°C
  Molar ratio, water : ethylene 0.25 : 1
  Circulating gas 1000 Nm$^3$/h per m$^3$ of catalyst
  Catalyst type: H$_3$PO$_4$ on acid-treated Bentonite supports per W. German Pat. No. 1,156,772

| By-Products: | |
|---|---|
| Diethyl ether | 5.00 wt-% |
| Hydrocarbons (up to C$_6$) | 0.01 wt-% |
| Acetaldehyde | 0.01 wt-% |
| Butanols | 0.01 wt-% |
| Others (polymers) | not detectable |

(b-2) Isopropanol Process (invention)
Reaction Conditions:
  Reaction pressure 40 atmospheres gauge
  Reaction temperature 160°C
  Molar ratio, water : propylene 0.15 : 1
  Circulating gas 800 Nm$^3$/h per m$^3$ of catalyst
  Catalyst type: H$_3$PO$_4$ on acid-treated Bentonite supports per W. German Pat. No. 1,156,772

| By-Products: | |
|---|---|
| Diisopropyl ether | 5.00 wt-% |
| Hydrocarbons (up to C$_6$) | 0.01 wt-% |
| Higher alcohols | 0.02 wt-% |
| Acetone | Traces |
| Others (polymers) | not detectable |

The above-described by-products are in each case contained in an alcohol and water mixture having the following approximate concentrations:

| | | |
|---|---|---|
| (a-1) | Ethanol concentration | 8–11 wt-% |
| (b-1) | Isopropanol concentration | 7–10 wt-% |
| (a-2) | Ethanol concentration | 23–27 wt-% |
| (b-2) | Isopropanol concentration | 23–27 wt-% |

EXAMPLE 2

The purification of alcohol mixtures as specified under a-2 and b-2 may be performed by extraction exclusively, as follows:

1. Ethanol process — Composition a-2

In an extraction column consisting of a total of 55 trays, raw ethanol with by-products is started on the 40th tray.

| The infeed is composed as follows: | | |
|---|---|---|
| Water | 5,838.0 kg/h | 73.75 wt-% |
| Ethanol | 1,980.0 kg/h | 25.00 wt-% |
| Diethyl ether | 99.0 kg/h | 1.25 wt-% |
| Hydrocarbons | 0.2 kg/h | 1.25 wt-% |
| Acetaldehyde | 0.2 kg/h | 1.25 wt-% |
| Butanols | 2.0 kg/h | 1.25 wt-% |

At the 55th tray washing water is fed in at 12.1 cubic meters per hour. The vapors leaving the top of the column are composed as follows:

| | | |
|---|---|---|
| Water | 1,050.0 kg/h | 88.5 wt-% |
| Ethanol | 35.6 kg/h | 3.0 wt-% |
| Hydrocarbons | 0.2 kg/h | — |
| Acetaldehyde | 0.2 kg/h | — |
| Butanol | 2.0 kg/h | 0.2 wt-% |
| Diethyl ether | 99.0 kg/h | 8.3 wt-% |

An aqueous solution of about 10.0% alcohol leaves the sump of the column:

| | | |
|---|---|---|
| Water | 16.868.1 kg/h | 89.7 wt-% |
| Ethanol | 1,944.1 kg/h | 10.3 wt-% |
| Other | Traces | |

2. Isopropanol Process — Composition b-2

For the isopropanol procedure the corresponding values appear as follows:

| Input | | |
|---|---|---|
| Water | 5,840.7 kg/g | 73.75 wt-% |
| Isopropanol | 1,980.1 kg/h | 25.00 wt-% |
| Diisopropyl ether | 99.0 kg/h | 1.25 wt-% |
| Hydrocarbons | 0.2 kg/h | — |
| n-Propanol | 0.2 kg/h | — |
| Hexanol | 0.2 kg/h | — |
| Acetone | not detectable | — |
| Wash Water water | 12,080.0 kg/h | — |
| Top Product | | |
| Water | 1,032.1 kg/h | 88.5 wt-% |
| Isopropanol | 35.0 kg/g | 3.0 wt-% |
| Diisopropyl ether | 99.0 kg/h | 8.5 wt-% |
| Hydrocarbons | 0.2 kg/h | — |
| Higher alcohols | 0.4 kg/h | — |
| Acetone | — | — |
| Sump Product | | |
| Water | 16,888.2 kg/h | 89.7 wt-% |
| Isopropanol | 1.945.1 kg/h | 10.3 wt-% |
| Other | traces | |

EXAMPLE 3

Mixtures, as specified under a-1 and b-1 cannot be purified by extraction alone, even with a considerably higher vapor output in the extraction column and consequently considerably greater alcohol losses at the top of the column. In the sump of the extraction column remain components which make purification absolutely necessary.

The sump product accordingly is not of sufficiently good quality.

EXAMPLE 4

The energy costs and the heat exchange surface areas for heating the reaction input stream or for cooling the reactor output mixture are much greater under the operating conditions of the prior art than they are under those of the invention, as is shown by the following example.

1. Ethanol Process a. At a molar water-to-ethylene ratio of 0.6 : 1, $$3.45 \times 10^6 \text{ kcal}/t$$

are required per ton of alcohol for the heating of the mixture entering the reactor from 60° to 280°C.

b. At a molar ratio of water to ethylene of only 0.25 : 1 and heating the reactor input mixture from 60° to only 220°C, $$2.24 \times 10^6 \text{kcal}/t$$

is required.

2. Isopropanol Process a. At a molar ratio of water to propylene of 0.4 : 1,

---

(a-1) Ethanol Process

| | Reaction Product Composition | | Wash Water |
|---|---|---|---|
| Water | 5,837.7 kg/h | 73.1 wt-% | 12,081.2 kg/h |
| Ethanol | 1,979.7 kg/h | 24.8 wt-% | — |
| Diethyl ether | 59.4 kg/h | 0.7 wt-% | — |
| Hydrocarbons | 29.7 kgβH | 0.4 wt-% | — |
| Acetaldehyde | 29.7 kg/h | 0.4 wt-% | — |
| Butanols | 19.8 kg/h | 0.2 wt-% | — |
| Polymers | 29.7 kg/h | 0.4 wt-% | — |

| | Top of Extraction Column | | Sump of Extraction Column | |
|---|---|---|---|---|
| Water | 962.0 kg/h | 64.2 wt-% | 16,956.0 kg/h | 91.4 wt-% |
| Ethanol | 375.0 kg/h | 25.0 wt-% | 1,604.7 kg/h | 8.6 wt-% |
| Diethyl ether | 59.4 kg/h | 4.0 wt-% | — | — |
| Hydrocarbons | 27.7 kg/h | 1.8 wt-% | 2.0 kg/h | — |
| Acetaldehyde | 29.5 kg/h | 2.0 wt-% | 0.2 kg/h | — |
| Butanol | 17.8 kg/h | 1.2 wt-% | 1.0 kg/h | — |
| Polymers | 27.7 kg/h | 1.8 wt-% | 2.0 kg/H | — |

The sump project accordingly is not of sufficiently good quality.

$$2.56 \times 10^6 \text{ kcal}/t$$

---

(b-1) Isopropanol Process

| | Reaction Product Composition | | Wash Water |
|---|---|---|---|
| Water | 5,840.7 kg/h | 73.3 wt-% | 12,079.6 kg/h |
| Isopropanol | 1,980.1 kg/h | 24.8 wt-% | |
| Diisopropyl ether | 59.4 kg/h | 0.7 wt-% | |
| Hydrocarbons | 39.6 kg/h | 0.5 wt-% | |
| Higher alcohols | 39.6 kg/h | 0.5 wt-% | |
| Acetone | 9.9 kg/h | 0.1 wt-% | |
| Polymers | 9.9 kg/g | 0.1 wt-% | |

| | Top of Extraction Column | | Sump of Extraction Column | |
|---|---|---|---|---|
| Water | 1000.3 kg/h | 66.6 wt-% | 16,920.0 kg/h | 91.4 wt-% |
| Isopropanol | 375.0 kg/h | 25.0 wt-% | 1,605.1 kg/h | 8.6 wt-% |
| Diisopropyl ether | 59.4 kg/h | 3.9 wt-% | — | — |
| Hydrocarbons | 35.6 kg/h | 2.4 wt-% | 4.0 kg/h | — |
| Higher alcohols | 9.9 kgβH | 0.7 wt-% | 29.7 kg/h | — |
| Acetone | 9.9 kg/h | 0.7 wt-% | — | — |
| Polymers | 9.9 kg/h | 0.7 wt-% | — | — | is required per ton of isopropanol for heating the reaction mixture from 90° to 240°C.

b. In heating the mixture for purposes of comparison from 90° to only 160°C and at a molar ratio of water to propylene of only 0.15 : 1, $1.33 \times 10^6$ kcal/$t$ is required.

From this it is shown that the process of the invention requires substantially less energy and smaller heat exchange surface areas.

EXAMPLE 5

By modifying in accordance with the invention the operating conditions in the reaction part of the apparatus and by recycling into the synthesis the by-products which are present in aqueous form the following increases in yield are obtained:

1. Ethanol Process

If the alcohol mixture produced is composed as in $a$-1, only 89.7 percent of the ethylene input has been transformed to alcohol. The remaining 10.3 percent of the ethylene is needed for the production of the specified by-products.

By comparison, if the process is modified in accordance with the invention by recycling the by-products and modifying the synthesis procedure, 99.85 percent of the ethylene is transformed to ethanol. The increase in yield therefore amounts to 10.15 percent.

2. Isopropanol Process

The comparative figures may be summarized as follows:

Without the recycling of the by-products, by proceeding at known temperatures and molar ratios of water to propylene, 10.9 percent of the propylene input is transformed into the desired isopropanol product.

With recycling, the yield is 99.9 percent so that here the yield of the process has been increased by 9 percent.

What is claimed is:

1. Process for the hydration of ethylene in the presence of phosphoric acid-containing supported catalysts to ethanol which comprises:
    a. carrying out the hydration in the vapor phase under conditions wherein the molar ratio of water to ethylene is in the range of about 0.1 to 0.3 : 1, the reaction temperature is in the range of about 190°–230°C, and the reaction pressure is in the range of about 60 to 80 atmopheres gauge, thereby forming a reaction product mixture containing unreacted ethylene steam volatile by-products and ethanol;
    b. separating unreacted gaseous ethylene from the reaction product mixture from (a);
    c. feeding the reaction product mixture from (b) to a washing extraction zone where said by-products are separated from said ethanol using 50 to 150 kg of steam per 100 liters of pure ethanol to vaporize said by-products which are removed overhead, said ethanol, free of said by-products, being withdrawn from the sump of said washing zone; and
    d. thereafter condensing the steam and volatilized by-products withdrawn overhead from the washing zone in step (c) and recycling same to hydration step (a) thereby supplying the water required for the hydration and increasing the concentration of the by-products which prevents the further formation of by-products in the hydration.

2. Process of claim 1 wherein dissolved ethylene in the reaction product mixture is separated in the washing extraction zone and is recycled to the hydration step.

3. Process for the hydration of propylene in the presence of phosphoric acid-containing supported catalysts to isopropanol which comprises:
    a. carrying out the hydration in the vapor phase under conditions wherein the molar ratio of water to propylene is in the range of about 0.1 to 0.2 : 1, the reaction temperatures are in the range formation about 140°–170°C and the reaction pressure is in the range of about 20–45 atmospheres gauge thereby forming a reaction product mixture containing unreacted propylene, steam-volatile by-products and is opropanol;
    b. separating unreacted gaseous propylene from the reaction product mixture from (a);
    c. feeding the reaction product mixture from (b) to a washing extraction zone wherein said by-products are separated from said isopropanol using 50 to 150 kg of steam per 100 liters of pure isopropanol to vaporize said by-products which are removed overhead, said isopropanol, free of said by-products, being withdrawn from the sump of said washing zone; and
    d. thereafter condensing the steam and by-products withdrawn overhead from the washing zone in step (c) and recycling same to the hydration step thereby supplying the water required for the hydration and increasing the concentration of the by-products which prevents further formation of by-products in the hydration.

4. Process of claim 3 wherein dissolved propylene in the reaction product mixture is separated in the washing extraction zone and is recycled to the hydration step.

* * * * *